(12) United States Patent
Wehba et al.

(10) Patent No.: US 8,660,860 B2
(45) Date of Patent: Feb. 25, 2014

(54) SYSTEM AND METHOD FOR SYNCHRONIZING MEDICATION CONFIGURATION INFORMATION AMONG SYSTEMS CONTAINING MEDICATION CONFIGURATION INFORMATION

(75) Inventors: Steven R. Wehba, Carlsbad, CA (US); Jeffrey E. Rinda, San Diego, CA (US); Patrick Ward, San Diego, CA (US)

(73) Assignee: Hospira, Inc., Lake Forest, IL (US)

( * ) Notice: Subject to any disclaimer, the term of this patent is extended or adjusted under 35 U.S.C. 154(b) by 598 days.

(21) Appl. No.: 12/265,470

(22) Filed: Nov. 5, 2008

(65) Prior Publication Data

US 2009/0125336 A1 May 14, 2009

Related U.S. Application Data

(60) Provisional application No. 60/986,968, filed on Nov. 9, 2007.

(51) Int. Cl.
*G06Q 50/00* (2012.01)
(52) U.S. Cl.
USPC .................................................. 705/3; 705/2
(58) Field of Classification Search
USPC .......................................................... 705/2
See application file for complete search history.

(56) References Cited

U.S. PATENT DOCUMENTS

| | | | |
|---|---|---|---|
| 5,681,285 A | 10/1997 | Ford et al. | |
| 6,269,340 B1 | 7/2001 | Ford et al. | |
| 2003/0014222 A1 | 1/2003 | Klass et al. | |
| 2004/0078231 A1 | 4/2004 | Wilkes et al. | |

(Continued)

FOREIGN PATENT DOCUMENTS

JP 2003296173 A 10/2003
WO 2005050526 A2 6/2005

OTHER PUBLICATIONS

Japanese Office Action, issued Jan. 29, 2013.

(Continued)

*Primary Examiner* — Hiep V Nguyen
(74) *Attorney, Agent, or Firm* — Michael R. Crabb

(57) ABSTRACT

A method and system for synchronizing medication configuration information. A primary medication configuration computer is adapted to receive medication configuration content from a medication configuration content source. The primary medication configuration computer is also adapted to generate medication configuration change information and transmit the medication configuration change information to an ancillary medication configuration computer, adapted to receive the medication configuration change information from the primary medication configuration computer. The ancillary medication configuration computer is also adapted to filter the medication configuration change information by applying a filtering rule to generate filtered medication configuration change information. The ancillary medication configuration computer is further adapted to store the filtered medication configuration change information in a repository and transmit at least a portion of the filtered medication configuration change information to a management client computer. The ancillary medication configuration computer is also adapted to receive an implementation decision about the portion of the filtered medication configuration change information, accepting or rejecting the portion of the filtered medication configuration change information. The ancillary medication configuration computer is also adapted to transmitting the accepted filtered medication configuration change information to an ancillary system database for integrating the accepted filtered medication configuration change information into the ancillary system database.

22 Claims, 12 Drawing Sheets

(56) References Cited

U.S. PATENT DOCUMENTS

| | | | |
|---|---|---|---|
| 2004/0172301 A1* | 9/2004 | Mihai et al. | 705/2 |
| 2005/0144043 A1 | 6/2005 | Holland et al. | |
| 2005/0278194 A1 | 12/2005 | Holland et al. | |
| 2006/0010098 A1* | 1/2006 | Goodnow et al. | 707/1 |
| 2006/0074633 A1 | 4/2006 | Mahesh et al. | |
| 2007/0116037 A1 | 5/2007 | Moore | |
| 2007/0213598 A1 | 9/2007 | Howard et al. | |
| 2007/0233520 A1 | 10/2007 | Wehba et al. | |
| 2008/0091466 A1 | 4/2008 | Butler et al. | |

OTHER PUBLICATIONS

Benjamin Mako Hill, Complete introduction to Ubuntu, Shoeisha Co., Ltd., Jun. 11, 2007, the First Edition, pp. 115 to 125.

Package Management in Debian GNU/Linux, Debian GNU/Linux Expert Desktop Use Special, Gijutsu-Hyohron Co., Ltd., Sep. 25, 2004, the First Edition, pp. 183 to 185.

European Application No. 08847611.4, Extended European Search Report Mailed on Sep. 16, 2013.

\* cited by examiner

| PENDING UPDATE | | ☒ |
|---|---|---|
| | UPDATE | EXISTING MEDICATION |
| GENERIC NAME: | ACETAMINOPHEN (EQ) | ACETAMINOPHEN (EQ) |
| BRAND NAME: | TYLENOL (EQ) | TYLENOL (EQ) |
| EXTERNAL ID: | 2173 | 2173 |
| NDC: | 007130164-12 | 007130164-12 |

| | AMOUNT: | UNIT: | AMOUNT: | UNIT: |
|---|---|---|---|---|
| STRENGTH: | 325 | MG | 325 | MG |
| VOLUME: | 1 | SUPP | 1 | SUPP |

THERAPEUTIC CLASS
 CODE: 28:08.92
 DESCRIPTION: ANALGESICS AND ANTIPYRETICS MISC.

| CODE | DESCRIPTION |
|---|---|
| 28:08.04 | NONSTEROIDAL ANTI-INFLAMMATOR... |
| 28:08.92 | ANALGESICS AND ANTIPYRETICES MISC. |
| 101 | OTHER |
| 40:12.00 | REPLACEMENT PREPARATIONS |
| THERID.1 | THERDESC.1 |

DOSAGE FORM
 CODE: SUPP  **
 DESCRIPTION: SUPP  **

| CODE | DESCRIPTION |
|---|---|
| LID LIQ | LID LIQ |
| ** | ** |
| SUPP | SUPP |
| IV BAG | IV BAG |
| 123 | BLAH |

| STATUS: | PENDING UPDATE | ACTIVE |
|---|---|---|
| SOURCE: | INTERFACE | INTERFACE |
| RECEIVED ON: | 05/30/2007 15:46 | 05/30/2007 11:47 |
| LAST EDITED ON: | | 05/30/2007 12:41 |
| LAST EDITED BY: | | MEDNET_ADMIN |

▲ ▼ (SKIP TO PREVIOUS OR NEXT IN LIST)   UPDATE  REJECT  CLOSE  HELP

FIG. 8

HOSPIRA MEDNET(R) MEDS (TM)

ACTION: UPDATED A PENDING MEDICATION

RECEIVED ON: 04 / 11 / 2007 13:59
UPDATED ON: 05 / 18 / 2007 08:43
UPDATED BY: PATRICK1
SOURCE: INTERFACE

ORIGINAL DEFINITION: — 1002
   GENERIC NAME: CEFEPIME
   BRAND NAME: MAXIPIME
   EXTERNAL ID: 2388
   NDC: 51479-0055-10
   STRENGTH: 2 GM
   VOLUME: 1 ADV
   THERAPEUTIC CLASS:
     CODE: 08:12.06
     DESCRIPTION: CEPHALOSPORINS
   DOSAGE FORM:
     CODE: ADV
     DESCRIPTION: ADV

FINAL DEFINITION: — 1004
   GENERIC NAME: CEFEPIME
   BRAND NAME: MAXIPIME
   EXTERNAL ID: 2388
   NDC: 51479-0055-20
   STRENGTH: 2 GM
   VOLUME: 100 ML
   THERAPEUTIC CLASS:
     CODE: 08:12.06
     DESCRIPTION: CEPHALOSPORINS
   DOSAGE FORM:
     CODE: BAG
     DESCRIPTION: BAG

CONFIGURE MEDICATION INTERFACE FILTER — 1102

☑ AUTOMATICALLY PRINT A RECEIPT WHENEVER A MEDICATION IS ADDED, EDITED, OR DELETED. — 1106

DOSAGE FORMS

| INCLUDE | CODE | DESCRIPTION |
|---|---|---|
| YES | INFSYR | INFSYR |
| NO | INH_AMP | INH_AMP |
| NO | INH_BTL | INH_BTL |
| NO | INH_VL | INH_VL |
| YES | IV_BAG | IV_BAG |
| YES | IV_BTL | IV_BTL |
| YES | IV_SYR | IV_SYR |
| NO | KIT | KIT |
| NO | LIQ | LIQ |
| NO | LOTION | LOTION |
| NO | MDI | MDI |

1104 — ADD   1112 — EDIT   DELETE — 1116

EXTERNAL IDs — 1110

| INCLUDE | ID |
|---|---|
| YES | 3153 |
| YES | 2874 |
| YES | 3108 |

1108 — ADD   1114 — EDIT   1118 — DELETE

1120 — SAVE   CANCEL   HELP

SYSTEM AND METHOD FOR SYNCHRONIZING MEDICATION CONFIGURATION INFORMATION AMONG SYSTEMS CONTAINING MEDICATION CONFIGURATION INFORMATION

CROSS-REFERENCE TO RELATED APPLICATIONS

This application claims the benefit of priority to U.S. Provisional Patent Application Ser. No. 60/986,968, filed Nov. 9, 2007, the entirety of which is hereby incorporated by reference.

FEDERALLY SPONSORED RESEARCH OR DEVELOPMENT

None.

TECHNICAL FIELD

The invention relates to systems and methods for synchronizing medication configuration information within a first system with medication configuration information within other systems. More particularly, the present invention relates to synchronizing medication configuration information within a centralized institution with medication configuration information within ancillary healthcare facility systems.

BACKGROUND OF THE INVENTION

Modern medical care often involves the use of electronic medical devices such as medication delivery pumps and/or patient condition monitors. Electronic medical pumps, for example, can be electronically loaded or configured with a customizable "drug library" containing certain drug delivery information or parameters, as disclosed in U.S. Pat. Nos. 5,681,285 and 6,269,340. Medication management systems for configuring, controlling, and monitoring medication delivery devices have been disclosed. For example, commonly owned U.S. patent application Ser. No. 10/930,358, which published as US20050144043A1 on Jun. 30, 2005 and U.S. patent application Ser. No. 10/783,573, which published as US20050278194A1 on Dec. 15, 2005, disclose a medication management system in which a user-customizable drug library or medication configuration information is prepared using a drug library editor (DLE) program and module of a medication management unit (MMU). The MMU downloads the customizable drug library to the medication delivery pump and receives status or activity information from the pump. Commonly owned U.S. patent application Ser. No. 10/783,877, which also published as WO2005050526A2 on Jun. 2, 2005, discloses how the drug library or medication configuration information is created, edited, stored and communicated to a medication delivery device in the context of a medication management system to deliver substances, such as fluids and/or fluid medication to patients. According to the above-mentioned commonly owned published patent applications, a typical medication management system, which can be considered an ancillary medication management system to a hospital information system (HIS) in a healthcare institution, includes a MMU in communication with one or more medication delivery devices. The MMU is a computer, typically a server, with an associated memory that stores the customized drug library or medication configuration information for configuring the medication delivery devices and the activity information received from the medication delivery devices.

Although the medication configuration information can be established (added, deleted, edited, etc.) in an ancillary medication management or delivery system, the medication configuration information is usually is established at a centralized location within a healthcare institution, such as within a pharmacy information system (PhIS) within an HIS. In the context of formulary medication configuration information, a Master Drug Formulary is used to configure Drug Libraries, as disclosed and described in commonly owned U.S. patent application Ser. No. 10/783,877, which published as US20070213598 A1 on Sep. 13, 2007. The '598 publication describes the content, format, transfer and many other details of the establishment of the medication configuration information and the transfer of this medication configuration information to ancillary medication management systems. As mentioned, commonly owned U.S. patent application Ser. No. 10/930,358, which published as US20050144043A1 on Jun. 30, 2005 also described the transfer and use of such medication configuration information, among other aspects.

Additions, deletions, edits, and/or modifications, together referred to as a changes, are made from time to time to the medication configuration information within the centralized system, such as the PhIS within an HIS. As mentioned, ancillary medication management systems can communicate with the PhIS within the HIS, and each ancillary medication management system has its own ancillary medication configuration information or drug library, which is typically a subset of the medication configuration information within the medication formulary at the HIS. However, ancillary medication management systems and the administrators of such systems do not always wish to implement one or more of these changes within their ancillary medication management systems, and need a mechanism to determine whether changes within medication configuration information within the centralized system should be implemented locally.

Thus, one objective of the present invention is the provision of at least a method, system and computer program product for synchronizing medication configuration information between a primary medication configuration information system and an ancillary medication management system and/or among ancillary medication management systems.

A further objective of the present invention is the provision of a flexible and customizable way to synchronize medication configuration information.

A further objective of the present invention is the provision of a way to synchronize only relevant medication configuration information to a particular ancillary medication management system.

All of the patents and patent application referred to within this Background of the Invention section of the present specification are hereby incorporated by reference and made a part of this specification. In addition, the present invention is provided to solve the problems discussed above and, to provide advantages and aspects not provided by medical systems, as well as achieve other objects not explicitly stated above. A full discussion of the features, advantages and objects of the present invention is deferred to the following detailed description, which proceeds with reference to the accompanying drawings.

SUMMARY OF THE INVENTION

The invention relates to systems and methods for synchronizing medication configuration information. Thus, in one embodiment, the present invention is directed to a system and method for synchronizing medication configuration information between a primary medication configuration computer and an ancillary medication configuration computer. The method includes receiving medication configuration change information from the primary medication configuration computer at the ancillary medication configuration computer.

The medication configuration change information is generated by the primary medication configuration computer in response to receiving medication configuration content from a medication configuration content source. In one embodiment, the medication configuration content source can include a pharmaceutical company wherein the company communicates configuration content to a healthcare institution, such as electronically transferring formulary medication information for new medications to the pharmacy computer or pharmacy information system (PhIS) of a healthcare institution. In another embodiment, the medication configuration content source can include a pharmacy client computer receiving changes, such as additions, deletions, and/or edits to formulary medication information from a pharmacy professional, and transferring such changed formulary medication information to the PhIS of a healthcare institution.

Once the medication configuration change information is received from the primary medication configuration computer at the ancillary medication configuration computer, the ancillary medication configuration computer is adapted to filter the medication configuration change information. The ancillary medication configuration computer or related system applies a filtering rule to generate filtered medication configuration change information.

In one embodiment, a filtering rules application or software module executing on within the ancillary medication configuration computer or related system, generates a filtering rules interface screen for receiving filtering rules. Through the filtering rules interface screen, a request can be transmitted to request entry of one or more filtering rules from the ancillary medication configuration computer, and the filtering rules can be received at the ancillary medication configuration computer for later use within the medication configuration information filtering process. In one embodiment, the filtering rules can include a dosage form and/or a medication identifier (ID).

Once the medication configuration information is filtered using one or more of the previously entered filtering rules, the filtered medication configuration change information is stored in a repository or "trap." The trap allows a ancillary system administrator to review and analyze all "trapped" filtered medication configuration change information prior to implementation or integration into the ancillary medication management system and respective database(s) therein. As such, in one embodiment, a repository management or trap management application or software module is provided for generating a trap management interface for receiving an implementation decision about the filtered medication configuration change information stored within the trap. The ancillary system administrator can use a management client computer through which the trap management interface can be used to accept or reject each filtered medication configuration change information entry within the trap. In one embodiment, when there is filtered medication configuration change information within the trap, or more than a predetermined amount of filtered medication configuration change information is within the trap, the trap management application can be configured to transmit a communication, such as an email, to the ancillary system administrator. The communication will notify ancillary system administrator that there is filtered medication configuration change information within the trap which must be acted on (accepted or rejected).

The accepted filtered medication configuration change information can then be transmitted to and integrated within an ancillary system database, such as a ancillary system formulary database and/or an ancillary clinical information system database, for use of the accepted filtered medication configuration change information within the ancillary system.

As indicated above, in one embodiment, the method and system of the present invention is directed to synchronizing formulary medication information between a primary medication configuration computer, such as a medication formulary computer or PhIS with a formulary medication database therein, and an ancillary medication configuration computer, such as a medication management system having a formulary medication database therein. In the context of medication formulary information changes can include additions of new formulary medications, deletions of formulary medications, or edits to existing formulary medications, such as edits to one or more of a generic name, brand name, external identifier, strength amount, strength units, volume amount, volume units, dosage form code, and/or dosage form description for each formulary medication.

In another embodiment, the medication configuration information can be used to assist in delivering medication through infusion pumps. In this embodiment, each medication configuration information or medication entry can include a generic name, brand name, rule set type, concentration, dosing units, lower hard limit, lower soft limit, upper soft limit, and/or upper hard limit for alarms, for delivering such medications through an infusion pump.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 8 is a pending update interface screen generated within the trap management application of one embodiment of the present invention.

FIG. 10 is a receipt confirming that a change to the medication configuration information was integrated into the ancillary medication management system of the present invention.

FIG. 11 is a configure filter rules interface screen generated within the filtering rules application of one embodiment of the present invention.

DETAILED DESCRIPTION

Figure 1:
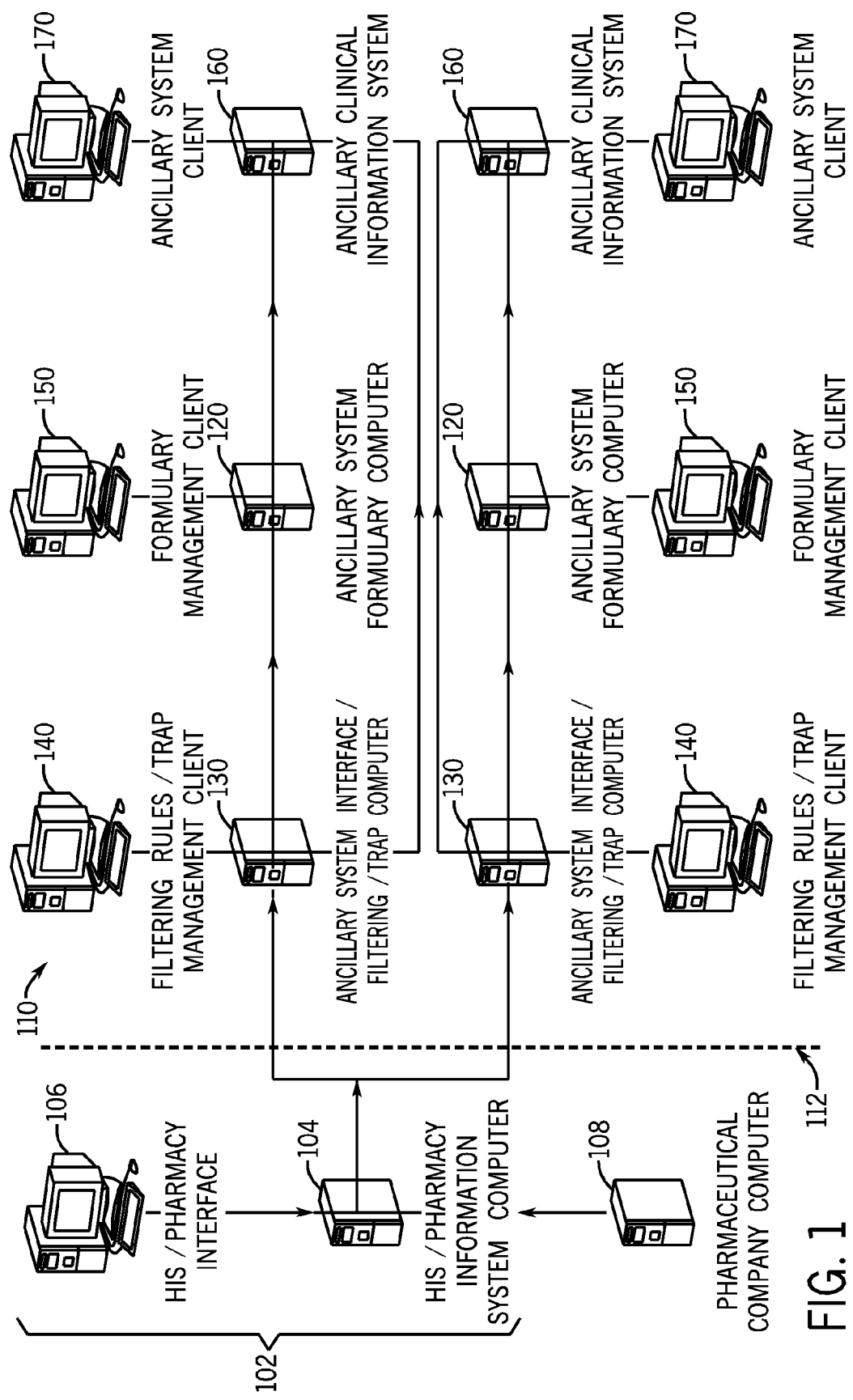
FIG. 1 is a system diagram of one embodiment of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 2:
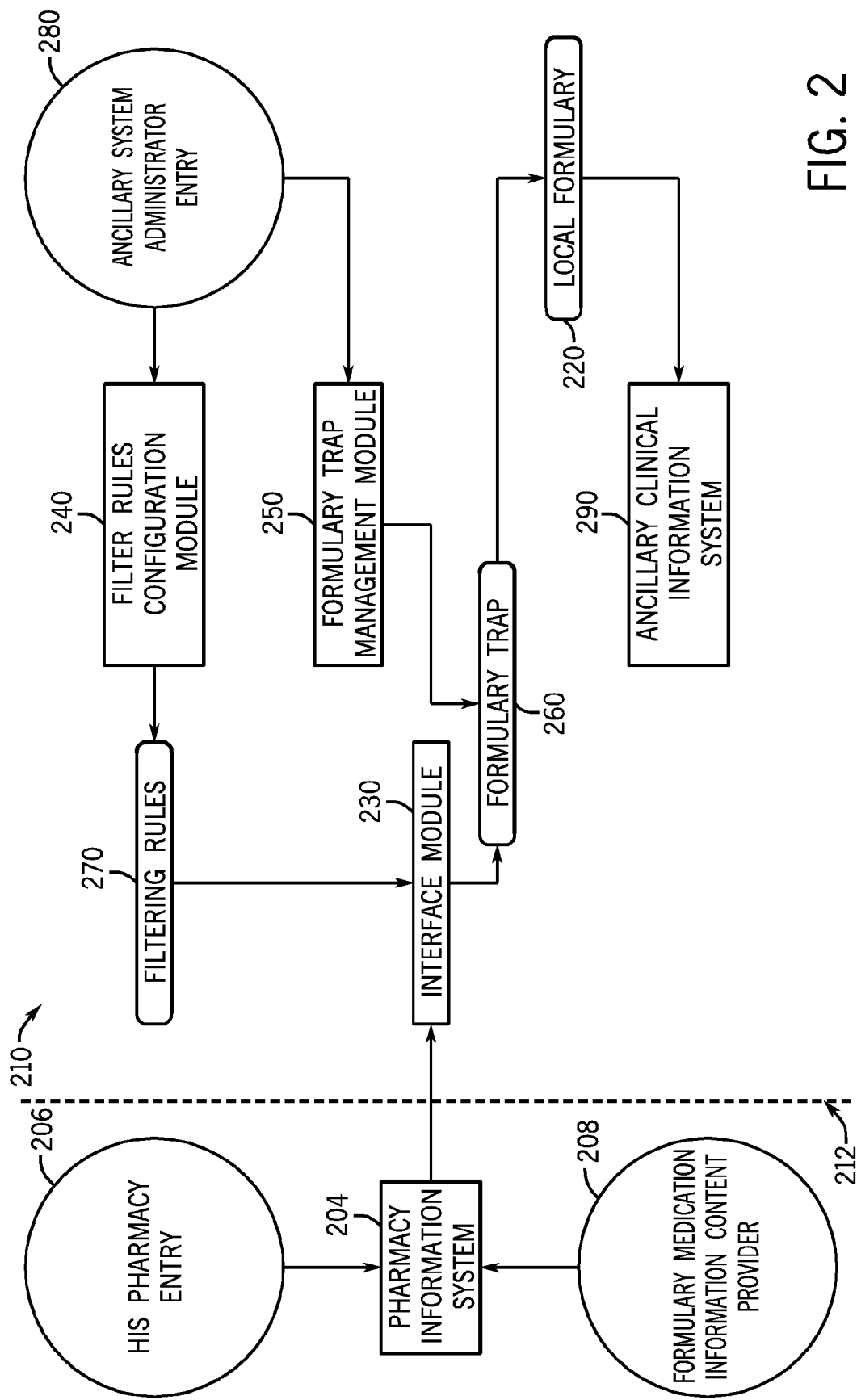
FIG. 2 is an functional diagram of one embodiment of the present invention.

Referring to FIG. 1, system diagram of one embodiment of the present invention is shown. A known centralized hospital information system (HIS) 102 is shown. Such systems are described in at least one or more of the above U.S. patent application referred to an incorporated herein. A primary medication configuration computer 104, such as a pharmacy information computer or system (PhIS) can a part of the HIS 102, or can be separate therefrom. Referring additionally to FIG. 2, a functional diagram of one embodiment of the present invention is shown. A pharmacy information system application 204 is shown. The PhIS computer 104 and pharmacy information system application 204, which can run therein are provided for receiving and storing medication configuration information, such as formulary medication information. This medication configuration information can be entered through a computer terminal 106, such as a pharmacy client computer or HIS/pharmacy interface terminal, by a pharmacist or other medication administration professional, shown in FIG. 2 as an HIS pharmacy entry function 206. The formulary medication information can also be received in electronic form from pharmaceutical companies, such as through a pharmaceutical company computer 108, which supply medications, such as pharmaceuticals, to the hospital or healthcare institution. This formulary medication information can be transmitted to the healthcare institution in various ways, such as by file transfer protocol (FTP), a file share posting and downloading therefrom, an electronic file attached to an email, or some other electronic means from the pharmaceutical company computer 108 to the primary medication configuration computer 104, as shown in FIG. 2 as entry function 208 by a Formulary Medication Information Content Provider. This formulary medication information can also be sent to the healthcare institution on a portable storage medium, such as on a CDROM or pen-drive from the Formulary Medication Information Content Provider, and entered through the HIS Pharmacy Entry function 206 using the HIS/Pharmacy Interface terminal 106.

The formulary medication information, received from a pharmaceutical company, or entered manually by medication administration professional, is used to update a formulary medication configuration information database 104 within the primary PhIS 20. Specifically, the received or entered formulary medication information is used to add new medication information entries, delete existing medication information entries, edit and/or modify existing medication information entries within the formulary medication information database 104 within the primary medication configuration computer or PhIS 104, 204. These data change actions are made from time to time to the formulary medication information within the formulary medication information database 104, typically on an ad hoc basis. In one embodiment, receipt of the medication configuration information can take place on a scheduled basis from other systems, such as from a Formulary Medication Information Content Provider shown at entry function 108.

These "master" medication configuration information entries within the medication configuration information database 104, 204 can be used to update or synchronize remote or ancillary medication management or delivery systems 110, 210, which are shown to the right of line 112 within FIG. 1 and functionally to the right of line 212 in FIG. 2. The ancillary systems can communicate with the primary medication information computer/PhIS 104, 204, and each ancillary system has its own "local" ancillary medication information, which is typically a subset of the medication configuration information stored within the primary medication information computer/PhIS 104, 204. In one embodiment, each "local" ancillary medication information, such as formulary medication information, is stored within an ancillary system formulary computer 120 and respective "local" formulary database 220 therein.

For each ancillary system, an ancillary medication configuration computer 130 is provided, which can perform several functions. Specifically, the ancillary medication configuration computer 130 can include an interface software module or application 230 for interfacing and communicating with the primary medication information computer/PhIS 104, 204. The ancillary medication configuration computer 130 can also include a filtering rules configuration software module or application 240 for configuring filtering rules as described herein. ancillary medication configuration computer 130 can also include a repository or "trap" management software module or application 250 for managing medication configuration information which is trapped or filtered into the repository or trap 260, which within the embodiment of FIG. 1 can also be a part of the ancillary medication configuration computer 130. Thus, the ancillary medication configuration computer 130 can also be considered an ancillary system interface/filtering/trap computer 130. The ancillary medication configuration computer 130 receives the medication configuration change information from the primary medication configuration computer 104. Once the medication configuration change information is received from the primary medication configuration computer 104, 204 at the ancillary medication configuration computer 130 and respective interface module 230, using filtering rules stored within a filtering rules repository 270, the ancillary medication configuration computer 130 and interface module 230 are adapted to filter the medication configuration change information according to the previously entered and configured filtering rules 270. As such, the ancillary medication configuration computer 130 applies one or more filtering rules to generate filtered medication configuration change information. The filtered medication configuration change information is trapped or filtered into and stored within the repository or trap 260.

The filtering rules within the filtering rules repository 270 can be created using the filtering rules application or software module 240 executing on within the ancillary medication configuration computer 130. The filtering rules module 240 and a client computer 140 can generate one or more filtering rules interface screens which can be displayed on the client computer 140 for receiving filtering rules from a local system pharmacist or ancillary system administrator, as indicated through entry function 280 within FIG. 2. As will be described in greater detail below, through the filtering rules interface screen, such as the screens shown in FIGS. 11-14, a request can be transmitted to request entry of one or more filtering rules from the ancillary medication configuration computer 130 and the filtering rules configuration module 240, the filtering rules can be entered through the client computer 140, and the filtering rules can be received at the ancillary medication configuration computer 130, for later use within the medication configuration information filtering process. Thus, the received filtering rules within the filtering rules repository 270 within the ancillary medication configuration computer 130 are used to filter the received medication configuration change information, and the filtered medication configuration change information is trapped or filtered into and stored within the repository or trap 260.

The trap 260 allows a pharmacist or ancillary system administrator to review and analyze all "trapped" filtered medication configuration change information, as shown by the entry function 280 within FIG. 2. In one embodiment, a repository management or trap management application or software module 250 is provided for managing trapped filtered medication configuration change information. In one embodiment, the trap management application 250 resides within executes on the ancillary medication configuration computer 130, and can generate one or more trap management interface screens, as shown in FIGS. 6-9, as will be described in greater detail below. The trap management interface screens can be provided through client computer 140, and allow the ancillary system administrator using these interface screens to provide an implementation decision about each of the filtered medication configuration change information stored within the trap, to the ancillary medication configuration computer 130 and the trap management application 260 running therein. The ancillary system administrator can use the client computer 140 and trap management interface screens to accept or reject each filtered medication configuration change information entry within the trap 260.

In one embodiment, when there is filtered medication configuration change information within the trap 260, or more than a predetermined amount of filtered medication configuration change information is within the trap 260, the trap management application 250 can be configured to transmit a communication, such as an email, to the ancillary system administrator through the client computer 140 or other computer or PDA being used by the ancillary system administrator. The communication will notify the ancillary system administrator that there is filtered medication configuration change information within the trap 260 which is ready to be or must be acted on (accepted or rejected). The trap management application 250 can be configured to summarize and/or categorize the filtered medication configuration change information that is within the trap 260, and include such summarization and/or categorization information as a part of the communication, such as an email, to the ancillary system administrator. For example, the trap management application 250 can be configured to separately determine and include the total number of "update", "addition," and/or "deletion," medication configuration information items within the trap 260, within the communication. Thus, the present invention provides an ancillary system administrator the ability to review, and accept or reject filtered medication configuration change information prior to implementation or integration of the filtered medication configuration change information into the ancillary medication management system or computer 120 and respective database(s) therein, such as a formulary medication database. Accepted and/or rejected filtered medication configuration change information can be tracked by the trap management application 250, and a history of such acceptances and rejections can be stored in the ancillary medication configuration computer 130.

Once the ancillary system administrator accepts one of more of the filtered medication configuration change information entries, the accepted filtered medication configuration change information can then be transmitted to and integrated within an ancillary system database, such as an ancillary clinical information system 290 and database therein. In the embodiment shown in FIG. 1, the accepted filtered medication configuration change information is transmitted to and integrated within a separate ancillary system formulary computer 120, and formulary database therein. From this ancillary computer formulary computer 120, various other local formulary and other medication management functions can be provided through a formulary management client 150, which can be more easily understood with reference to the patents and applications referenced within Background of the Invention section of the present specification. Specifically, a local Drug Library Editor (DLE), more recently referred to as RXRULES and MedNetMeds by the Assignee of the present invention, and associated functions, can be provided through the formulary management client 150.

A subset or more of the local formulary medication database within the ancillary system formulary computer 120 can be communicated to or downloaded to the ancillary clinical information system 160. The ancillary clinical information system 160 can include one or more medication management units (MMUs), which are described in detail within the patents and applications referenced within the Background of the Invention section of the present specification. An ancillary system client 170 can be provided for interfacing with the ancillary clinical information system 160 and MMUs therein. The use of the local formulary medication database information within MMUs and connected systems and devices can be understood from these referenced patents and applications. Alternatively, the accepted filtered medication configuration change information can be transmitted and integrated directly within the ancillary clinical information system 160 as shown in FIG. 1.

The synchronizing system and method for the primary and ancillary systems 102, 110 and the applications therein, can be implemented in software, firmware, hardware, or a combination thereof. In one mode, the synchronizing system and method for the primary and ancillary systems 102, 110 is implemented in software, as one or more executable programs or applications, and is executed by one or more special or general purpose digital computer(s), such as a personal computer (PC; IBM-compatible, APPLE-compatible, or otherwise), personal digital assistant, workstation, minicomputer, server, and/or mainframe computer. Therefore, the primary and/or the ancillary system computers 104, 106, 120, 130, 140, 150, 160, and 170 may be representative of any computers in which the applications of the synchronizing system and method for the primary and ancillary systems 102, 110 resides or partially resides.

Generally, in terms of hardware architecture, as shown in FIGS. 1 and 2, the computers 104, 106, 120, 130, 140, 150, 160, and 170 of the primary and ancillary systems 102, 110, as well as the pharmaceutical computer 108, include a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the other computer components.

The processors are hardware devices for executing software, particularly software stored in memory. The processors can be any custom made or commercially available processor, a central processing unit (CPU), an auxiliary processor among several processors associated with the computers 104, 106, 120, 130, 140, 150, 160, and 170 of the primary and ancillary systems 102, 110, as well as the pharmaceutical computer 108, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, EJB, CORBA, and DCOM. In one embodiment, the PhIS computer 104 is a WINDOWS based server or series of servers and the ancillary configuration information computers 130 are each a WINDOWS based server or series of servers.

Each memory of each computer 104, 106, 120, 130, 140, 150, 160, and 170 of the primary and ancillary systems 102, 110, as well as the pharmaceutical computer 108 can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, these memories may incorporate electronic, magnetic, optical, and/or other types of storage media. The memories can have a distributed architecture where various components are situated remote from one another, but are still accessed by the processors of the computers 104, 106, 120, 130, 140, 150, 160, and 170 of the primary and ancillary systems 102, 110, as well as the pharmaceutical computer 108.

The software within one or more of the above referenced memories may include one or more separate programs. The separate programs comprise ordered listings of executable instructions for implementing logical functions. In the examples of FIGS. 1 and 2, the software in the memories includes suitable operating systems (O/S). A non-exhaustive list of examples of suitable commercially available operating systems is as follows: (a) a WINDOWS operating system available from Microsoft Corporation; (b) a NETWARE operating system available from Novell, Inc.; (c) a MACINTOSH operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time VXWORKS operating system from WindRiver Systems, Inc.; or (g) an appliance-based operating system, such as that implemented in handheld computers or personal digital assistants (PDAs) (e.g., PalmOS™ available from Palm Computing, Inc., and WINDOWS CE available from Microsoft Corporation). The operating systems essentially control the execution of other computer programs, such as the configuration/activity information aggregation application and/or the configuration information application, in accordance with the present invention, and provide scheduling, input-output control, file and data management, memory management, and communication control and related services.

The pharmacy information system application 204, the interface application 230, the filtering rules configuration application 240, the trap management application 250, and other source programs within the primary and ancillary synchronizing system 102, 110 may be a source program, executable program (object code), script, or any other entity comprising a set of instructions to be performed. When a source program, the program needs to be translated via a compiler, assembler, interpreter, or the like, which may or may not be included within the memories, so as to operate properly in connection with the O/S. Furthermore, these applications can be written as (a) an object oriented programming language, which has classes of data and methods, or (b) a procedural programming language, which has routines, subroutines, and/or functions, for example but not limited to, VB.Net, C#, C, C++, Pascal, Basic, Fortran, Cobol, Perl, Java, and Ada. In one embodiment, the configuration/activity information aggregation application is written in VB.Net and the configuration information application is written in T-SQL.

The I/O devices referred to above may include input devices, for example input modules for PLCs, a keyboard, mouse, scanner, microphone, touch screens, interfaces for various medical devices, bar code readers, stylus, laser readers, radio-frequency device readers, etc. Furthermore, the I/O devices may also include output devices, for example but not limited to, output modules for PLCs, a printer, bar code printers, displays, etc. Finally, the I/O devices may further include devices that communicate both inputs and outputs, for instance but not limited to, a modulator/demodulator (modem; for accessing another device, system, or network), a radio frequency (RF) or other transceiver, a telephonic interface, a bridge, and a router.

If the computers 104, 106, 120, 130, 140, 150, 160, and 170 of the primary and ancillary systems 102, 110, as well as the pharmaceutical computer 108, are a PC, workstation, PDA, or the like, the software in the respective memories may further include a basic input output system (BIOS) (not shown in FIGS. 1 and 2). The BIOS is a set of essential software routines that initialize and test hardware at startup, start the O/S, and support the transfer of data among the hardware devices. The BIOS is stored in ROM so that the BIOS can be executed when computers 104, 106, 120, 130, 140, 150, 160, and 170 of the primary and ancillary systems 102, 110, as well as the pharmaceutical computer 108 are activated.

When the computers 104, 106, 120, 130, 140, 150, 160, and 170 of the primary and ancillary systems 102, 110, as well as the pharmaceutical computer 108, are in operation, the processors therein are configured to execute software stored within respective memories, to communicate data to and from memories, and to generally control operations of the computers 104, 106, 120, 130, 140, 150, 160, and 170 of the primary and ancillary systems 102, 110, as well as the pharmaceutical computer 108, pursuant to the software. The configuration/activity information aggregation application and the configuration information applications, and the O/S, in whole or in part, but typically the latter, are read by respective processors, perhaps buffered within the processors, and then executed.

When the synchronizing system and method for the primary and ancillary systems 102, 110 are implemented in software, as is shown in FIGS. 1 and 2, it should be noted that the application programs therein can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The application programs, such as the pharmacy information system application 204, the interface application 230, the filtering rules configuration application 240, the trap management application 250 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the synchronizing system and method for the primary and ancillary systems 102, 110 are implemented in hardware, these systems and methods can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 3:
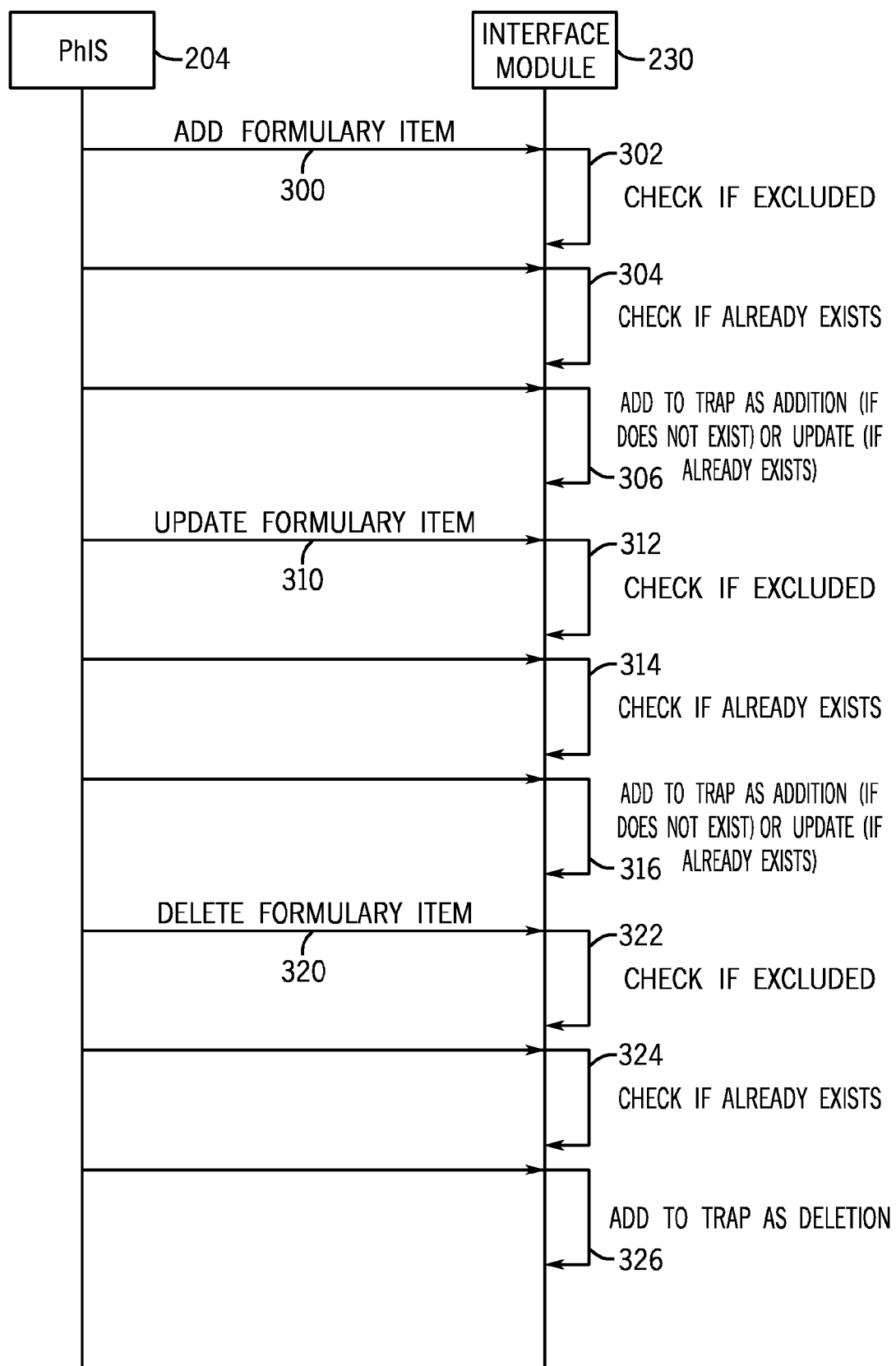
FIG. 3 is a flow diagram of one embodiment of the process of receiving changes to the medication configuration information of the present invention.

Referring to FIG. 3, one embodiment of the process of receiving changes to the medication configuration information is shown in a flow diagram format. Specifically, FIG. 3 shows some of interactions between the PhIS 204 and the interface application 230. In a first step 300, the PhIS 204 can send an "add formulary item" to the interface application 230 for adding a new formulary medication to the ancillary system. In a second step 302, the interface module is adapted to check whether the item should be excluded from the trap 260, based on a previously entered filtering rule. If the item should be excluded, the interface module will not forward the item along to the trap 260. If the interface module does not determine that the item should be excluded, then at a third step 304, the interface module is adapted to determine if the item already exists in the medication configuration information within the ancillary system, such as within a local medication formulary 220. If the item does not exist in the medication configuration information within the ancillary system, at a fourth step 306, the interface module is adapted to send the item to the trap 260 with a designation of an "addition." If the item does exist in the medication configuration information within the ancillary system, at the fourth step 306, the interface module is adapted to send the item to the trap 260 with a designation of an "update."

In a fifth step 310, the PhIS 204 can send an "update formulary item" to the interface application 230 for updating an existing formulary medication in the ancillary system. In a sixth step 312, the interface module is adapted to check whether the item should be excluded from the trap, based on a previously entered filtering rule. If the item should be excluded, the interface module will not forward the item along to the trap 260. If the interface module does not determine that the item should be excluded, then at a seventh step 314, the interface module is adapted to determine if the item already exists in the medication configuration information within the ancillary system, such as within a local medication formulary 220. If the item does not exist in the medication configuration information within the ancillary system, at a eighth step 316, the interface module is adapted to send the item to the trap 260 with a designation of an "addition." If the item does exist in the medication configuration information within the ancillary system, at the ninth step 316, the interface module is adapted to send the item to the trap 260 with a designation of an "update."

In a tenth step 320, the PhIS 204 can send an "delete formulary item" to the interface application 230 for deleting an existing formulary medication in the ancillary system. In a eleventh step 322, the interface module is adapted to check whether the item should be excluded from the trap, based on a previously entered filtering rule. If the item should be excluded, the interface module will not forward the item along to the trap 260. If the interface module does not determine that the item should be excluded, then at a twelfth step 324, the interface module is adapted to determine if the item already exists in the medication configuration information within the ancillary system, such as within a local medication formulary 220. If the item does not exist in the medication configuration information within the ancillary system, at a thirteenth step 326, the interface module is adapted to take no action. If the item does exist in the medication configuration information within the ancillary system, at the thirteenth step 326, the interface module is adapted to send the item to the trap 260 with a designation of an "deletion."

Figure 4:
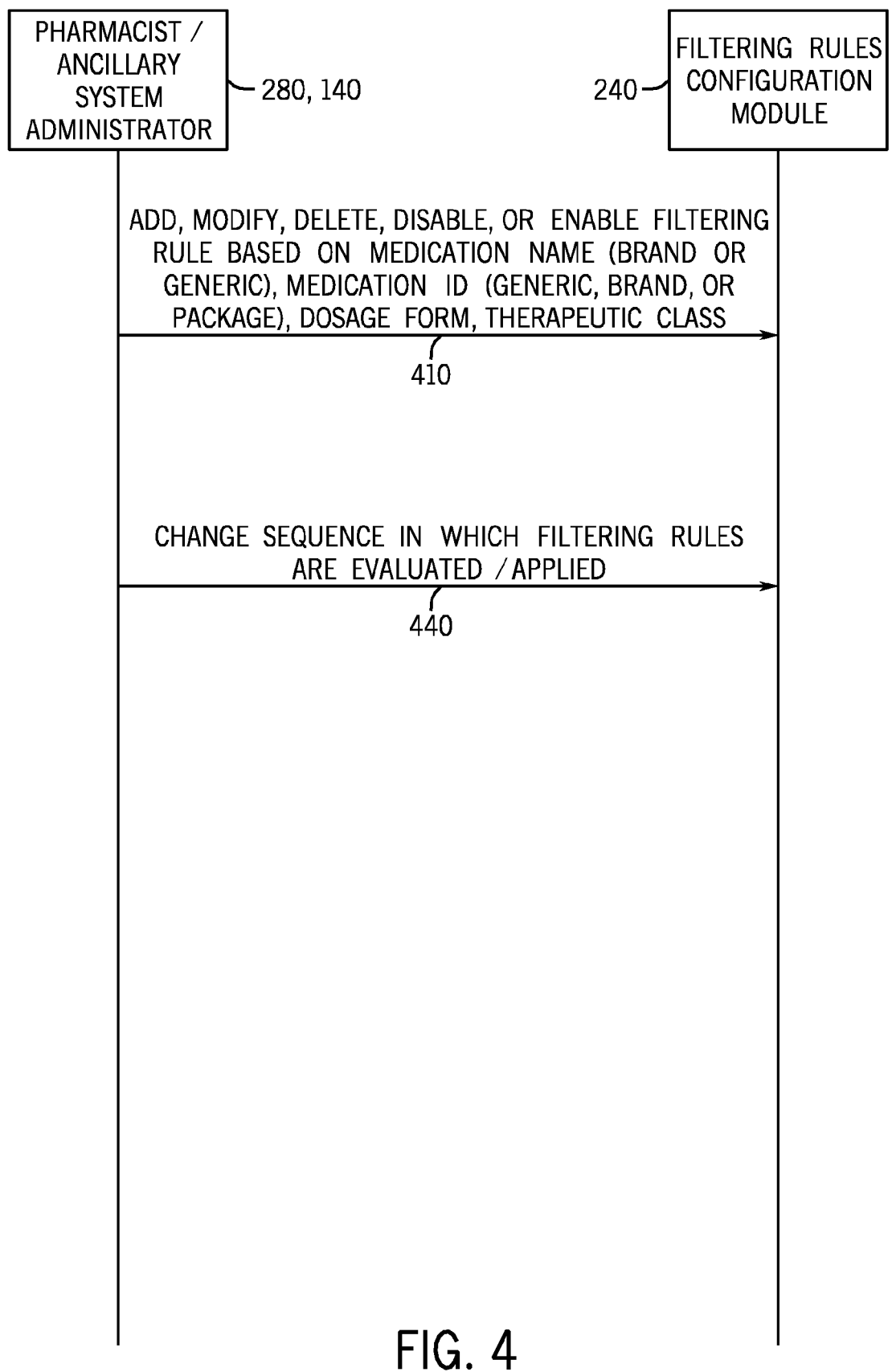
FIG. 4 is a flow diagram of one embodiment of the process of configuring filtering rules used to filter changes to the medication configuration information of the present invention.

Referring to FIG. 4, one embodiment of the process of configuring filtering rules used to filter changes to the medication configuration information is shown in a flow diagram format. Specifically, FIG. 4 shows some of the interactions between the client computer 140, with a pharmacist/ancillary system administrator using such client computer 140, and the filtering rules configuration application 240. In a first set of steps 410, which each can be a separate step, the pharmacist/ancillary system administrator using such client computer 140, and one or more interface screens generated at least in part by the filtering rules configuration application 240, can cause the client computer 140 to send an "add", "modify", "delete", and "enable" command for a filtering rule to respectively "add", "modify", "delete", and "enable" a filtering rule. Each filtering rule can be based on either one or more of a medication name, such as a generic name and/or a brand name, an external identifier/medication identifier (ID) (i.e., generic, brand or package ID), a strength amount, strength units, volume amount, volume units, dosage form code, dosage form description for each formulary medication, and/or a therapeutic class. In another embodiment, the filtering rules can be can be based on configuration information which can be used to assist in delivering medication through infusion pumps. In this embodiment, the filtering rules can be based on a generic name, brand name, rule set type, concentration, dosing units, lower hard limit, lower soft limit, upper soft limit, and/or upper hard limit for alarms, for delivering such medications through an infusion pump. In a second set of steps 440 shown in FIG. 4, which each can be a separate step, the pharmacist/ancillary system administrator using the client computer 140, and one or more interface screens generated at least in part by the filtering rules configuration application 240, can cause the client computer 140 to send a change or set sequence command for a filtering rule to respectively designate the sequence that such rule should be applied to the medication configuration information items received from the PhIS 204. For example, a filtering rule can be designated as applying "first" when the medication configuration information items received from the PhIS 204. The filtering rules, once configured by the pharmacist/ancillary system administrator using the client computer 140 and interacting with the filtering rules configuration application 240, are stored in the filtering rules repository 270 for use by the interface application 230 as described herein.

In one embodiment, a integration engine software application sold under the name RHAPSODY by ORION HEALTH of New Zealand, also having offices in Santa Monica, Calif., can be used to assist in the interfacing functions between the primary and ancillary systems 102, 110, and can also be used to assist in performing the filtering functions described herein. Information about the RHAPSODY software application can be found at www.orionhealth.com/rhapsody/index.htm. In one embodiment, RHAPSODY version 2.4.2 (with Administrator 2.4.3) can be used.

Figure 5:
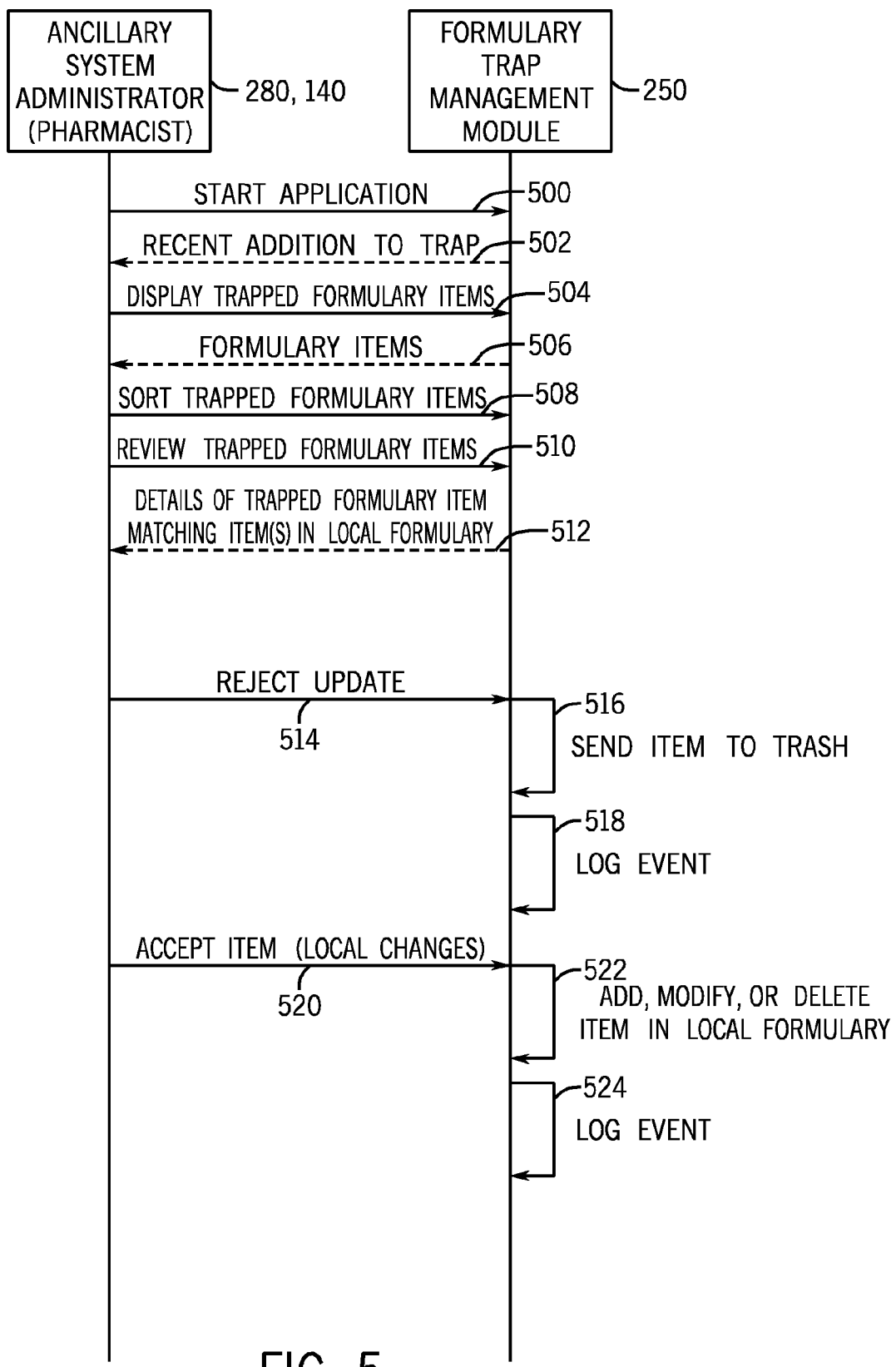
FIG. 5 is a flow diagram of one embodiment of the process of managing the filtered changes to the medication configuration information within the trap of the present invention.

Referring to FIG. 5, one embodiment of the process of managing the filtered changes to the medication configuration information within the trap is shown in a flow diagram format. Specifically, FIG. 5 shows some of the interactions between the client computer 140, with a pharmacist/ancillary system administrator using such client computer 140, and the trap management application 250. In a first step 500, the pharmacist/ancillary system administrator using the client computer 140, and one or more interface screens generated at least in part by the trap management application 250, can cause the client computer 140 to send an start application command to the trap management application 250 for initiating a trap management session. In a second step 502, the trap management application 250 can respond to the first step 500 by sending or communicating a list of medication configuration information items that have recently been added to the trap 260 (i.e., since the last session, since a specific date, or within a specific time frame), to the client computer 140 through an interface screen generated at least in part by the trap management application 250. This list allows the pharmacist/ancillary system administrator to view, review and take action on the medication configuration information items that are in the trap 260, as is described herein.

In a third step 504, the pharmacist/ancillary system administrator using the client computer 140, and one or more interface screens generated at least in part by the trap management application 250, can cause the client computer 140 to send a display trapped items command to the trap management application 250 for displaying the medication configuration information items that are in the trap 260 on the client computer 140. In a fourth step 506, the trap management application 250 can respond to the third step 504 by sending or communicating a list of medication configuration information items that have been added to the trap 260, to the client computer 140 through an interface screen generated at least in part by the trap management application 250. Again, this list allows the pharmacist/ancillary system administrator to view, review and take action on the medication configuration information items that are in the trap 260, as is described herein. In any of these embodiments, the pharmacist/ancillary system administrator using the client computer 140 can request that the medication configuration information items be displayed by pending medications, active medications, or pending and active medications combined, with any generic name or external ID, generic names beginning with (any character), or external IDs beginning with (any character), to name just a few examples.

Once the list of medication configuration information items is shown on the client computer 140, in a fifth step 508, the pharmacist/ancillary system administrator using the client computer 140, and one or more interface screens generated at least in part by the trap management application 250, can cause the client computer 140 to send a sort trapped items command to the trap management application 250 for sorting the medication configuration information items that are in the trap 260 on the client computer 140. In one embodiment, and also as shown in FIG. 6, the pharmacist/ancillary system administrator using the client computer 140 can request that the medication configuration information items be sorted, and displayed in order, by generic name, brand name, external ID, strength, volume, dosage form, received/updated date/time, or item status.

Figure 7:
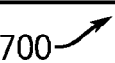
FIG. 7 is a pending addition interface screen generated within the trap management application of one embodiment of the present invention.
Figure 9:
FIG. 9 is a pending deletion interface screen generated within the trap management application of one embodiment of the present invention.

In a sixth step 510, the pharmacist/ancillary system administrator using the client computer 140, and one or more interface screens generated at least in part by the trap management application 250, can cause the client computer 140 to send a review item command to the trap management application 250 for reviewing more details about any particular medication configuration information item that is within the trap 260 on the client computer 140. In a seventh step 512, and as shown in FIGS. 7-9, the trap management application 250 can respond to the sixth step 510 by sending or communicating more detailed medication configuration information for a selected medication configuration information item that have been added to the trap 260, to the client computer 140 through an interface screen generated at least in part by the trap management application 250. This detailed information allows the pharmacist/ancillary system administrator to view, review and take action on the selected medication configuration information item. Specifically, at an eighth step 514, the pharmacist/ancillary system administrator using the client computer 140, and one or more interface screens, as shown for example in FIG. 8, and generated at least in part by the trap management application 250, can cause the client computer 140 to send a "reject update" command (for a selected "update" item) to the trap management application 250 for rejecting the item and preventing the item from being integrated within the local formulary 220. Thus, at a ninth step 516, the trap management application 250 responds to the eighth step 514 by sending or communicating the item to the trash bin (it deletes it from the trap). At a tenth step 518, the trap management application 250 can also respond to the eighth step 514 by logging, tracking/storing this action, including the type of action taken and the time and date the action was taken. Alternatively, at an eleventh step 520, the pharmacist/ancillary system administrator using the client computer 140, and one or more interface screens, as shown for example in FIGS. 7-9, and generated at least in part by the trap management application 250, can cause the client computer 140 to send a "accept" command (for a selected item) to the trap management application 250 for accepting the item and causing the item to be integrated within the local formulary 220. At a twelfth step 522, the trap management application 250 responds to the eleventh step 520 by adding, deleting, or modifying the item in the local formulary 220, according to the type of item ("addition" item, "deletion" item, or "update" item, respectively). At a thirteenth step 524, the trap management application 250 can also respond to the eleventh step 520 by logging, tracking/storing this action, including the type of action taken and the time and date the action was taken.

In one embodiment, if a new medication configuration information item is received from the primary system, such as the PhIS 104, 204, and the new medication configuration information item is not filtered out by any of the filtering rules 270, and the trap 260 already includes an existing medication configuration information item for that medication, then the interface application 230 can be configured to overwrite the existing medication configuration information item with the new medication configuration information item within the trap 260. In addition, the ancillary systems 210 and applications therein are configured to track and store an "audit trail" of all filtering rules and changes thereto, all received medication configuration information items and exclusions from the trap 260, all received medication configuration information items and inclusions to the trap 260, all actions taken as a part of the management of the trapped medication configuration information items, as well as all transmissions from of medication configuration information items from the trap to a local repository, such as a local formulary 220. This audit trail can be used to perform various comparisons, and one or more of the applications within the ancillary system 210 can be used to perform such comparisons. For example, the one or more of the applications within the ancillary system 210 can be configured to compare actual suggested changes within a medication configuration information item received from the primary system 102, with the medication configuration information item the ends up being used within the local repository, such as the local formulary 220. In one particular example, the pharmacist/ancillary system administrator may make edits to trapped medication configuration information items, and these edits modify the medication configuration information item which actually ends up being used within the local repository, such as the local formulary 220. The one or more of the applications within the ancillary system 210 can be configured to determine if any such changes took place, the type of medication configuration information within each medication configuration information item that is changed, how often such changes took place, as compared to the overall number of medication configuration information items transmitted to the local repository, such as the local formulary 220, among many other comparisons. Many other comparisons and reports providing information on such comparisons come to mind, in view of the present specification, with reference to U.S. patent application Ser. No. 11/873,269, filed Oct. 16, 2007, entitled SYSTEM AND METHOD FOR COMPARING AND UTILIZING ACTIVITY INFORMATION AND CONFIGURATION INFORMATION FROM MULTIPLE MEDICAL DEVICE MANAGEMENT SYSTEMS, which is hereby incorporated by reference herein.

Figure 6:
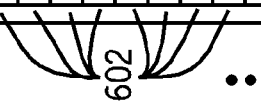
FIG. 6 is a pending medications interface screen generated within the trap management application of one embodiment of the present invention.

Referring to FIG. 6, a pending medications interface screen 600 depicts the medication configuration information items 602 which have been received by the trap 260, but which have not yet been acted on by the pharmacist/ancillary system administrator. As previously indicated, the pending medications interface screen 600 allows the pharmacist/ancillary system administrator using the client computer 140 to display and sort the medication configuration information items 602 by generic name, brand name, external ID, strength, volume, dosage form, received/updated date/time, or item status. In one embodiment, clicking on the heading of a column shown in FIG. 6 will re-sort the items 602 in the pending medications interface screen 600 according to the information about the items 602 in that column. The trap management application 250 can also be configured for the pending medications interface screen 600 to display the medication configuration information items 602 in different colors, having specific meanings. In one embodiment, the trap management application 250 can be configured to display "active" medication configuration information items 602 in black, "pending addition" medication configuration information items 602 in blue, "pending update" medication configuration information items 602 in green, and "pending deletion" medication configuration information items 602 in red. A "show" drop down menu 610 can be used to display and select one of pending medications, active medications, and pending and active medications. A "with" drop down menu 620 can be used to display and select one of any generic name or external ID, generic names beginning with (any character), and external IDs beginning with (any character). Once a selection is made from each of the "show" and "with" menus, a refresh button 630 can be used to refresh the screen and show the items 602 which fall within the combined selection. Items 602 can be imported into and exported from the pending medications interface screen 600 as well. In order to view more details about any one item 602, the pharmacist/ancillary system administrator can select or "double click" on an item 602 from within the pending medications interface screen 600.

Referring to FIG. 7, pending addition interface screen 700 depicts more details about a selected "addition" item 602 from the pending medications interface screen 600. Various specific information about the item 602 is shown, such as generic name, brand name, external ID, NDC, strength, volume, therapeutic class, therapeutic code and therapeutic description, dosage form, dosage code, dosage description, status of the item 602, source of the item 602, when the item was received and editing information. An "add" button 702 is provided for the pharmacist/ancillary system administrator to select to add, transmit and integrate the item 602 to the local formulary 220. A "reject" button 704 is provided for the pharmacist/ancillary system administrator to select to reject the item 602 and prevent it from being added or transmitted to the local formulary 220.

Referring to FIG. 8, pending update interface screen 800 depicts more details about a selected "update" item 602 from the pending medications interface screen 600. Again, various specific information about the item 602 is shown, such as generic name, brand name, external ID, NDC, strength, volume, therapeutic class, therapeutic code and therapeutic description, dosage form, dosage code, dosage description, status of the item 602, source of the item 602, when the item was received and editing information. Since the action is to "update" an existing item, the right side of the pending update interface screen 800 also shows the existing information for that item within the local formulary 220, for comparison purposes. An "update" button 802 is provided for the pharmacist/ancillary system administrator to select to update, transmit and integrate the update information for the item 602 to the local formulary 220. A "reject" button 804 is provided for the pharmacist/ancillary system administrator to select to reject the "update" item 602 and prevent it from being used to modify the local formulary 220.

Referring to FIG. 9, pending deletion interface screen 900 depicts more details about a selected "deletion" item 602 from the pending medications interface screen 600. Again, various specific information about the item 602 is shown, such as generic name, brand name, external ID, NDC, strength, volume, therapeutic class, therapeutic code and therapeutic description, dosage form, dosage code, dosage description, status of the item 602, source of the item 602, when the item was received and editing information. An "delete" button 902 is provided for the pharmacist/ancillary system administrator to select to delete and remove the item 602 from the local formulary 220. A "reject" button 904 is provided for the pharmacist/ancillary system administrator to select to reject the "delete" item 602 request and prevent the delete action from taking effect in the local formulary 220. In one embodiment, the user level and security level of the pharmacist/ancillary system administrator login information can be implemented in a manner to only allow certain pharmacist/ancillary system administrators having predetermined security levels to view certain types of medication configuration information items within the pending medications interface screen 600 and/or perform only certain predetermined actions on certain predetermined types of medication configuration information items 602.

In each of at least the pending addition and pending update interface screens 700, 800, many of the details and fields for such details of each medication configuration information item being proposed for implementation can be edited and/or modified by the pharmacist/ancillary system administrator using the client computer 140. For example, for the medication configuration information item shown in the pending addition interface screen 700 in FIG. 7, the pharmacist/ancillary system administrator is provided the ability to modify at least the generic name, the brand name, the external ID, the strength amount and units, the volume amount and units, the selected therapeutic class code and description, and the selected dosage form code and description. Within this example, the NDC is not modifiable. In this way, the pharmacist/ancillary system administrator is provided significant flexibility is implementing an their healthcare institution's preferences.

In each of the pending addition, pending update, and pending interface screens 700, 800, 900, the pharmacist/ancillary system administrator using the client computer 140 accepts the medication configuration information item being proposed for implementation can press the "add", "update" or "delete" buttons 702, 802, 902, respectively, to accept the item, as is or as modified by the pharmacist/ancillary system administrator. When the pharmacist/ancillary system administrator presses any of the "add", "update" or "delete" buttons 702, 802, 902, the status for the respective item in the respective pending addition, pending update, and pending interface screens 700, 800, 900, and within the trap 260, changes from "pending" to "active." The trap management can also be configured to cause this status to change from "pending" to "active" when the pharmacist/ancillary system administrator using the client computer 140 makes any modifications to the medication configuration information item.

In another embodiment, instead of the pharmacist/ancillary system administrator manually managing the medication configuration information items within the trap 260 through the client computer 140 and respective interface screens described herein, the trap management application 250 can be configured to automatically accept, reject, and/or modify each medication configuration information item received within the trap 260 using particular predetermined acceptance, rejection, and/or modification criteria. The criteria can be a range of, or can be a, specific number(s), letter(s), code(s), or other criteria using one or more of the details about each of the medication configuration information items. Alternatively, the ancillary systems 270 do not need to have a trap management application 250, and automatic implementation of additional or different filtering rules could be performed.

Referring to FIG. 11, a configure filter rules interface screen 1100 is shown. This configure filter rules interface screen 1100 is launched by pressing a "Preferences" button 640 within the pending medications interface screen 600 shown in FIG. 6. A pharmacist/ancillary system administrator must have a predetermined necessary user level within the ancillary system 1100 to use the client computer 140 to gain access to at least the configure filter rules interface screen 1100. The configure filter rules interface screen is generated by the filtering rules configuration application 240, and allows the pharmacist/ancillary system administrator using the client computer 140 to review the current filtering rules that are in effect, add new rules, delete existing rules, and mark existing rules as being included or not included for use by the interface application 230 during the filtering process. In the embodiment shown within configure filter rules interface screen 1100 of FIG. 11, "dosage form" filtering rules and "external ID" filtering rules can be added and implemented by the pharmacist/ancillary system administrator to filter the medication configuration information. However, other filtering rules easily come to mind based on the present specification, such as other details of each medication configuration information, as presented in at least FIGS. 6-9.

Figure 12:
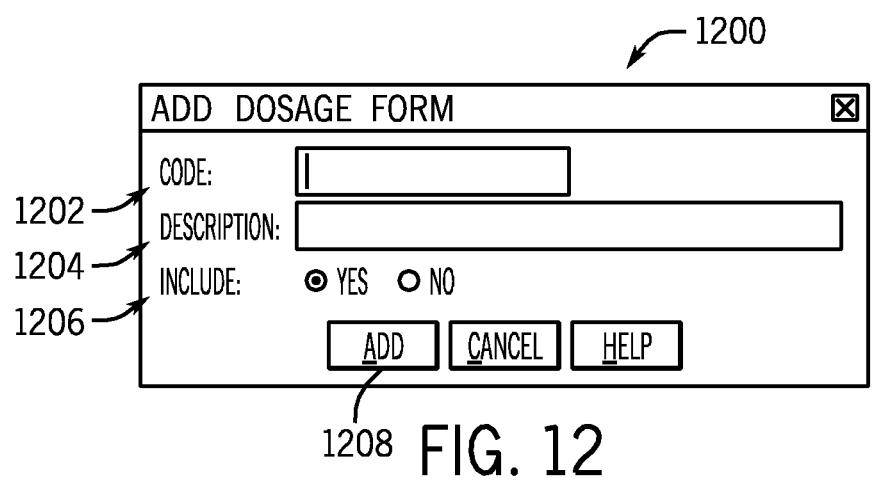
FIG. 12 is an add dosage form filtering rule interface screen generated within the filtering rules application of one embodiment of the present invention.

In the embodiment in FIG. 11, if the pharmacist/ancillary system administrator wishes to add a dosage form filtering rule, the configure filter rules interface screen 1100 provides an "add" button 1104 to do so. When the pharmacist/ancillary system administrator presses the add button 1104 using client computer 140, an add dosage form filtering rule interface screen 1200, shown in FIG. 12, is generated within the filtering rules application 240 and on the display of the client computer 140. The add dosage form filtering rule interface screen 1200 includes a code field 1202, a description field 1204 and "include" yes and no selection 1206. The code field 1202 allows the pharmacist/ancillary system administrator to enter a dosage form code. The description field 1204 allows the pharmacist/ancillary system administrator to enter a dosage form description. The "include" yes and no selection 1206 allows the pharmacist/ancillary system administrator to selected either "yes" or "no" to include or not to include, respectively, such dosage form filtering rule to be use in filtering by the interface application 230. Once the pharmacist/ancillary system administrator has entered/selected this information, an "add" button 1208 is provided to allow the pharmacist/ancillary system administrator click on this button to add the entered dosage form filter to the dosage forms filters 1106, as shown in the configure filter rules interface screen 1100 within FIG. 1.

Figure 13:
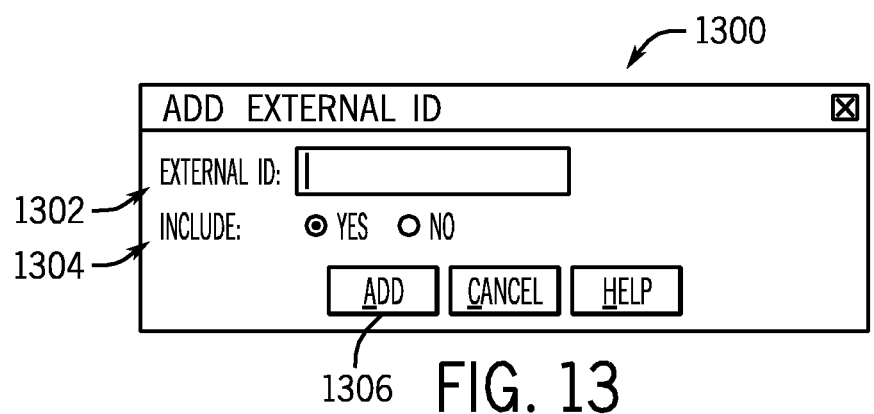
FIG. 13 is an add external ID filtering rule interface screen generated within the filtering rules application of one embodiment of the present invention.

Likewise, in the embodiment in FIG. 11, if the pharmacist/ancillary system administrator wishes to add an external ID filtering rule, the configure filter rules interface screen 1100 provides another "add" button 1108 to do so. When the pharmacist/ancillary system administrator presses the add button 1108 using client computer 140, an add external ID filtering rule interface screen 1300, shown in FIG. 13, is generated within the filtering rules application 240 and on the display of the client computer 140. The add external ID filtering rule interface screen 1300 includes an external ID field 1302 and an "include" yes and no selection 1304. The external ID field 1302 allows the pharmacist/ancillary system administrator to enter an external identifier or ID. The "include" yes and no selection 1304 allows the pharmacist/ancillary system administrator to selected either "yes" or "no" to include or not to include, respectively, such external ID filtering rule to be use in filtering by the interface application 230. Once the pharmacist/ancillary system administrator has entered/selected this information, an "add" button 1306 is provided to allow the pharmacist/ancillary system administrator click on this button to add the entered external ID filter to the external ID filters 1110, as shown in the configure filter rules interface screen 1100 within FIG. 11.

Thus, using interface screens, such as the interface screens shown in FIGS. 12 and 13, the pharmacist/ancillary system administrator can add new filtering rules to the filtering rules repository 270. In addition, in the embodiment shown in FIG. 11, the configure filtering rules interface screen 1100 provides an edit dosage forms button 1112 and an edit external ID button 1114 for editing previously added dosage form filtering rules and external ID filtering rules, respectively. This allows the pharmacist/ancillary system administrator to select a dosage form or external ID filtering rule from the dosage form filters 1106 or external ID filters 1110, and then click on from the respective edit button 1112, 1114 to edit the selected filtering rule. Likewise, in the embodiment shown in FIG. 11, the configure filtering rules interface screen 1100 provides a delete dosage forms button 1116 and a delete external ID button 1118 for deleting previously added dosage form filtering rules and external ID filtering rules, respectively, in a similar manner. Once all edit are made to the filtering rules, the configure filtering rules interface screen 1100 provides a save button 1120 saving additions, edits, and deletions made during the session, to the filtering rules repository 270, for use by the interface application 230 in filtering medication configuration information received from the primary medication configuration information system.

The configure filter rules interface screen 1100 also has a receipt check off box 1102 that allows the pharmacist/ancillary system administrator to select to cause a receipt, such as the receipt 1000 shown in FIG. 10, to print each time an item 602 is added, deleted, or updated, or identified for being added, deleted, or updated, to the local repository, such as the local formulary 220. The example in FIG. 10 shows an "update" to a medication configuration information item, including the original definition 1002 of the medication configuration information item, and the final definition 1004 of the medication configuration information item.

In one embodiment, the user level and security level of the pharmacist/ancillary system administrator login information can be implemented in a manner to only allow certain pharmacist/ancillary system administrators having specific predetermined security levels to access the configure filter rules interface screen 1100 and the filtering rules therein, and/or to only allow certain pharmacist/ancillary system administrators having specific predetermined security levels to access, add/modify/delete certain types of filtering rules.

In one exemplary embodiment of the present invention, a particular messaging format is used for sending medical configuration information from the PhIS 104, 204 to the ancillary system computers 130 and the interface application 230 therein. Specifically, the following tables provide representative HL7 formatted information that would be received by the interface application 230. It should be understood that several other data message formats could be used, such as XML. The HL7 data format divides up a message into segments. The structure of one embodiment of a medication configuration information message, entitled a formulary maintenance transaction (FMT) the message structure includes MSH . . . MFI . . . MFE . . . ZFM, as will be better understood with reference to the below tables.

The MSH segment of the message is standard header information that identifies the sending system or system that is sending the message, the receiving system or system that will be receiving the message, the message type, a timestamp, and an encoding format, as follows:

| MSH—Message Header Segment | | | |
|---|---|---|---|
| MSH | MSH | R | 3 |
| 1 Field Separator | \| | R | 1 |
| 2 Encoding characters | ˆ~\& | R | 4 |
| 3 Sending Application | Host application | R | 15 |
| Field 4 not used | | | |
| 5 Receiving application | HOSPIRARX | R | 15 |
| Field 6 not used | | | |
| 7 Date/Time of message | EFA/EFD timestamp | O | 26 |
| Field 8 not used | | | |
| 9 Message type | MFN | R | 7 |
| Field 10 not used | | | |
| 11 Processing ID | P | R | 1 |
| 12 Version ID | 2.3 | R | 8 |
| 13 Sequence number | Sequence number | O | 15 |

The MFI segment of the message corresponds to the external identifier (ID), as used herein, as follows:

| MFI—Master File Identification Segment | | | |
|---|---|---|---|
| MFI | MFI | R | 3 |
| 1 Master File Identifier | Site Specific | R | 12 |

The MFE segment of the message identifies what to do with the medication configuration information update. The format of this particular sending process or method embodiment can only identify an add/update item and a delete item. It does not differentiate between add and update. Other embodiments are possible. The following provides the format of this particular segment:

| MFE—Master File Entry segment | | | |
|---|---|---|---|
| MFE | MFE | R | 3 |
| 1 Record level event code | MAD—Formulary add/update MDL—Formulary delete | R | 12 |
| 2 Active Indicator | A—Active I—Inactive | R | 1 |
| 3 Site Indicator | Bit string | R | 10 |

The ZFM segment of the message specifies all the details about the medication configuration information. The interface application 230 uses this information, along with the external ID to perform filtering using the filtering rule 270.

| ZFM - Formulary maintenance segment | | | |
|---|---|---|---|
| ZFM | ZFM | R | 3 |
| 1 Formulary code | A, C or D (add, change, or delete) | R | 1 |
| 2 Medication ID | CDM Number | R | 15 |
| 3 Generic name | Generic name of medication | R | 30 |
| 4 Medication class | Medication class (DEA) | R | 1 |
| 5 Alternate Med ID | RX Drug Code # | R | 15 |
| 6 Not Used | Not used | O | 15 |
| 7 Brand Name | Medication Brand Name | O | 30 |
| 8 Dosage Form | i.e. tablet, capsule | R | 10 |
| 9 Strength | Numeric strength of item | O | 12 |
| 10 Strength units | ex. mg, G, mcg | O | 10 |
| 11 Volume | Numeric volume of item | O | 8 |

-continued

| ZFM - Formulary maintenance segment | | | | |
|---|---|---|---|---|
| ZFM | ZFM | | R | 3 |
| 12 Volume units | ex ml., L | | O | 5 |
| 13 Alternate med ID2 | NDC # | | O | 15 |
| 14 Therapeutic class | Therapeutic class Description (Class = 20 characters; Description = 80 characters) | | O | 100 |
| 15 Not Used | Not Used | | O | 15 |
| 16 GCN Sequence Number | GCN Sequence Number | | O | 10 |
| 17 Manufacturer | Manufacturer | | O | 15 |
| 18 Not Used | Not Used | | O | 15 |
| 19 Order from supplier | Numeric value of order | | O | 15 |
| 20 Units of order from supplier | ex ml., L | | O | 10 |
| 21 Package form from supplier | i.e. tablet, capsule | | O | 10 |

The following provides one example of an HL7 Formulary Maintenance Transaction (FMT) message framed with an SOB (011) and EOB (028), <CR> (TCP/IP protocol):

```
<SOB>
MSH|^~\&|SMS| |HOSPIRARX| |200703130854| |MFN| |P|2.3|<CR>
MFI|PDM<CR>
MFE|MAD|A|0001<CR>
ZFM|A|11223344|CIMETIDINE|0|2211||TAGAMET|TAB|300|MG|
1|TAB|12345-6789-01|56:40^INSULINS||30100|SLK||3|MG|TAB<CR>
<EOB>
<CR>
```

The following table shows one embodiment of the interface application 230 determines if an incoming message should result in an addition, update, or deletion, or if the incoming message should be rejected entirely, within the filtering process. For instance, the first row represents the following: if there is no corresponding formulary item in the ancillary system database or local formulary 220, and the incoming message says "add", there is no need to compare anything further, the formulary item will be inserted into the "trap" 260 as a "pending addition." As another example, the fourth row represents the following: if there is already a pending addition in the trap 260 that corresponds to the new message using both identity fields (e.g. ID and name), and the new message is an "add" message, the new message will be rejected (i.e. ignored).

| Interface Application Message Processing | | | | |
|---|---|---|---|---|
| Status of Most Recent Record in Database* | Incoming Message "Formulary Code" | Primary "significant Field" evaluation result | Secondary "Significant Field" evaluation result | Message action |
| None | A | Not needed | Not needed | Pending addition |
| None | C | Not needed | Not needed | Pending addition |
| None | D | Not needed | Not needed | Rejected |
| Pending addition | A | Identical | Identical | Rejected |
| Pending addition | C | Identical | Identical | Rejected |
| Pending addition | D | Identical | Identical | Pending deletion |
| Pending change | A | Identical | Identical | Rejected |
| Pending change | C | Identical | Identical | Rejected |
| Pending change | D | Identical | Identical | Pending deletion |
| Pending delete | A | Identical | Identical | Pending change |
| Pending delete | C | Identical | Identical | Rejected |
| Pending delete | D | Identical | Identical | Rejected |
| Pending addition | A | Identical | Different | Update most recent record |
| Pending addition | C | Identical | Different | Update most recent record |
| Pending addition | D | Identical | Different | Update most recent record |
| Pending change | A | Identical | Different | Update most recent record |
| Pending change | C | Identical | Different | Update most recent record |
| Pending change | D | Identical | Different | Update most recent record |
| Pending delete | A | Identical | Different | Update most recent record |
| Pending delete | C | Identical | Different | Update most recent record |
| Pending delete | D | Identical | Different | Update most recent record |
| Pending addition | A | Different | Not needed | Pending change |
| Pending addition | C | Different | Not needed | Pending change |
| Pending addition | D | Different | Not needed | Pending deletion |
| Pending change | A | Different | Not needed | Pending change |
| Pending change | C | Different | Not needed | Pending change |
| Pending change | D | Different | Not needed | Pending deletion |
| Pending delete | A | Different | Not needed | Pending change |
| Pending delete | C | Different | Not needed | Pending change |
| Pending delete | D | Different | Not needed | Pending deletion |
| Active | A | Identical | Identical | Rejected |
| Active | C | Identical | Identical | Rejected |
| Active | D | Identical | Identical | Pending deletion |
| Active | A | Identical | Different | Update most recent record |
| Active | C | Identical | Different | Update most recent record |
| Active | D | Identical | Different | Pending deletion |
| Active | A | Different | Not needed | Pending change |
| Active | C | Different | Not needed | Pending change |
| Active | D | Different | Not needed | Pending deletion |

Interface Application Message Processing

| Status of Most Recent Record in Database* | Incoming Message "Formulary Code" | Primary "significant Field" evaluation result | Secondary "Significant Field" evaluation result | Message action |
|---|---|---|---|---|
| Deleted | A | Identical | Not needed | Pending addition |
| Deleted | C | Identical | Not needed | Rejected |
| Deleted | D | Identical | Not needed | Rejected |
| Deleted | A | Different | Not needed | Pending addition |
| Deleted | C | Different | Not needed | Rejected |
| Deleted | D | Different | Not needed | Rejected |

*Records explicitly rejected by the MedNet Meds user are not evaluated

In one embodiment, the primary medication configuration computer 104, and application 204 therein, such as a PhIS 104, 204 can be configured to track and store the identification and other specific information about all of the different ancillary systems 110 that should receive medication configuration change information from the primary medication configuration computer 104, and application 204 therein. Such ancillary system identification information can include a TCP/IP address, a protocol format, an facility name, and other data necessary to send such medication configuration change information to the ancillary medication configuration computer 130, as one of ordinary skill in the art would understand. Thus, when the primary medication configuration computer 104, and application 204 receives medication configuration change information from other systems, such as content provider 208, or such information is manually entered, the primary medication configuration computer 104, and application 204 will know which ancillary medication configuration computer(s) to send such medication configuration change information, and will have the necessary data about the ancillary medication configuration computer 130 to do so.

In a related yet further embodiment, the primary medication configuration computer 104, and application 204 therein, such as a PhIS 104, 204 can be configured to utilized the above-mentioned tracked stored information about the ancillary systems 110 and ancillary medication configuration computers 130, and to be able to differentiate between and among the different ancillary systems 110 to send only certain medication configuration change information to one or more ancillary systems 110, and to send only certain other medication configuration change information to one or more other ancillary systems 110. This determination that is performed at and by the primary medication configuration computer 104, and application 204 therein, such as a PhIS 104, 204 can be based on various predetermined criteria, such as generic name, brand name, external identifier, strength amount, strength units, volume amount, volume units, dosage form code, dosage form description, rule set type, concentration, dosing units, lower hard limit, lower soft limit, upper soft limit, upper hard limit.

It should be emphasized that the above-described embodiments of the present invention are examples of implementations, and are merely set forth for a clear understanding of the principles of the invention. Many variations and modifications may be made to the above-described embodiment(s) of the invention without substantially departing from the principles of the invention. All such modifications are intended to be included herein within the scope of this disclosure and by the following claims.

What is claimed is:

1. A method of synchronizing medication configuration information between a primary medication configuration computer and an ancillary medication configuration computer, comprising the steps of:
   receiving medication configuration change information from the primary medication configuration computer at the ancillary medication configuration computer;
   applying a filtering rule to generate an include information set comprising medication change configuration information that meets a predetermined set of criteria;
   determining, based on the filtering rule, that the include information set should not be excluded from a management client computer;
   determining that the include information set has corresponding medication configuration information already stored in a repository at the ancillary medication configuration computer;
   overwriting the corresponding medication configuration information with the include information set to generate updated medication configuration information; and,
   transmitting at least a portion of the updated medication configuration information from the ancillary medication configuration computer to the management client computer.

2. The method of claim 1 wherein the medication configuration information is formulary medication information.

3. The method of claim 1 wherein the primary medication configuration computer is a centralized healthcare institution computer comprising a medication formulary computer.

4. The method of claim 1 wherein the ancillary medication configuration computer performs the step of applying the filtering rule to generate the include information set.

5. The method of claim 1 further comprising the steps of:
   transmitting a request to enter the filtering rule from the ancillary medication configuration computer; and,
   receiving the filtering rule at the ancillary medication configuration computer.

6. The method of claim 1 further comprising the step of:
   generating a filtering rules interface screen for receiving the filtering rule at the ancillary medication configuration computer.

7. The method of claim 1 further comprising the step of:
   receiving an implementation decision regarding the include information set at the ancillary medication configuration computer from the management client computer.

8. The method of claim 7 wherein the implementation decision comprises accepting the include information set to establish an accepted filtered medication configuration change information.

9. The method of claim 8 further comprising the step of:
transmitting the accepted filtered medication configuration change information to at least one of an ancillary system formulary database and an ancillary clinical information system database; and,
integrating the accepted filtered medication configuration change information into the at least one of the ancillary system formulary database and the ancillary clinical information system database.

10. The method of claim 1 wherein the medication configuration information comprises formulary medication information.

11. The method of claim 10 wherein the formulary medication information is selected from a group consisting of generic name, brand name, external identifier, strength amount, strength units, volume amount, volume units, dosage form code, and dosage form description.

12. The method of claim 1 wherein the medication configuration information is selected from a group consisting of generic name, brand name, rule set type, concentration, dosing units, lower hard limit, lower soft limit, upper soft limit, and upper hard limit.

13. The method of claim 1 wherein the filtering rule is selected from a group consisting of a dosage form and a medication identifier.

14. The method of claim 1 wherein the predetermined filtering criteria comprise a dosage form or a medication identifier.

15. The method of claim 14 wherein the dosage form includes one of a dosage form code and a dosage form description.

16. A system for synchronizing medication configuration information comprising:
a primary medication configuration computer adapted to receive medication configuration content from a medication configuration content source, adapted to generate medication configuration change information, and adapted to transmit the medication configuration change information; and,
an ancillary medication configuration computer adapted to receive medication configuration change information from the primary medication configuration computer, and adapted to:
apply a filtering rule to generate an include information set comprising medication change configuration information that meets a predetermined set of criteria,
determine, based on the filtering rule, that the include information set should not be excluded from a management client computer,
determine that the include information set has corresponding medication configuration information already stored in a repository,
overwrite the corresponding medication configuration information with the include information set to generate updated medication configuration information, and
transmit at least a portion of the updated medication configuration information to the management client computer.

17. A system for synchronizing medication configuration information comprising:
a primary medication configuration computer comprising a pharmacy application adapted to receive medication configuration content comprising formulary medication information, wherein the pharmacy application is adapted to generate medication configuration change information and transmit the medication configuration change information; and,
an ancillary medication configuration computer comprising an interface application adapted to receive medication configuration change information from the primary medication configuration computer, the ancillary configuration computer further comprising a filtering application adapted to filter the medication configuration change information by applying a filtering rule to generate an include information set comprising medication change configuration information that meets a predetermined set of criteria, wherein the ancillary medication configuration computer is further adapted to:
determine, based on the filtering rule, that the include information set should not be excluded from a management client computer, and
determine that the include information set has corresponding medication configuration information already stored in a repository,
wherein the ancillary medication configuration computer further comprises a repository management application adapted to:
overwrite the corresponding medication configuration information with the include information set to generate updated medication configuration information, and
transmit at least a portion of the updated medication configuration information to the management client computer for receiving an implementation decision about the updated medication configuration information.

18. A computer program product for synchronizing medication configuration information between a primary medication configuration computer and an ancillary medication configuration computer, comprising a non-transitory computer readable medium encoded with software comprising:
a first code segment for receiving medication configuration change information from the primary medication configuration computer at the ancillary medication configuration computer;
a second code segment for applying a filtering rule to generate an include information set comprising medication change configuration information that meets a predetermined set of criteria;
a third code segment for, based on the filtering rule, determining that the include information set should not be excluded from a management client computer;
a fourth code segment for determining that the include information set has corresponding medication configuration information already stored in a repository;
a fifth code segment for overwriting the corresponding medication configuration information with the include information set to generate update medication configuration information; and,
a sixth code segment for transmitting at least a portion of the updated medication configuration information to the management client computer.

19. The computer program product of claim 18 further comprising: a seventh code segment for transmitting a request to enter the filtering rule from the ancillary medication configuration computer; and,
an eighth code segment for receiving the filtering rule at the ancillary medication configuration computer.

20. The computer program product of claim 18 further comprising: a ninth code segment for generating a filtering rules interface screen for receiving the filtering rule at the ancillary medication configuration computer.

21. The computer program product of claim 18 further comprising:
    a tenth code segment for receiving an implementation decision accepting the include information set at the ancillary medication configuration computer from the management client computer.

22. The computer program product of claim 21 further comprising:
    an eleventh code segment for transmitting the accepted include information set to at least one of an ancillary system formulary database; and,
    a twelfth code segment for integrating the accepted include information set into the ancillary system formulary database.

* * * * *